United States Patent [19]

Sekiya et al.

[11] Patent Number: 5,302,764
[45] Date of Patent: Apr. 12, 1994

[54] PROCESS FOR PREPARING TRIFLUOROHYDROCARBON COMPOUND

[75] Inventors: Akira Sekiya; Shigeru Kurosawa, both of Tsukuba; Toshiro Yamada, Fujisawa; Kuniaki Goto, Setagaya, all of Japan

[73] Assignees: Japan as represented by Director General of Agency of Industrial Science & Technology; Nippon Zeon Co., Ltd., Tokyo, Japan

[21] Appl. No.: 849,076
[22] PCT Filed: Aug. 28, 1991
[86] PCT No.: PCT/JP91/01140
§ 371 Date: Jun. 29, 1992
§ 102(e) Date: Jun. 29, 1992
[87] PCT Pub. No.: WO92/03397
PCT Pub. Date: Mar. 5, 1992

[30] Foreign Application Priority Data

Aug. 28, 1990 [JP] Japan .................. 2-227531

[51] Int. Cl.$^5$ .................. C07C 17/10; C07C 19/02; C07C 19/08
[52] U.S. Cl. .................. 570/123; 570/134
[58] Field of Search .................. 570/123

[56] References Cited

U.S. PATENT DOCUMENTS 2,521,626  9/1950  Benning .................. 570/123
2,568,660  9/1951  Rosen .................. 570/123
2,759,026  8/1956  McCleary .................. 570/123

FOREIGN PATENT DOCUMENTS 48-505  1/1973  Japan .

OTHER PUBLICATIONS

R. E. Banks, Journal of Fluorine Chemistry, 33 (1986) pp. 227-346.

Primary Examiner—Joseph E. Evans
Attorney, Agent, or Firm—Birch, Stewart, Kolasch & Birch

[57] ABSTRACT

A difluorinated hydrocarbon compound represented by the general formula (1) is reacted with cobalt trifluoride to give a trifluorinated hydrocarbon compound represented by the general formula (2), wherein R represents lower alkyl and R' and R" represent each hydrogen, halogen or lower alkyl which may be halogenated. The reacton proceeds under mild conditions to yield the objective compound with high selectivity.

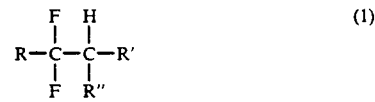

(1)

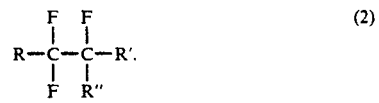

(2)

11 Claims, No Drawings invention will be specifically described by the following examples.

REFERENTIAL EXAMPLE

To 351 milli-moles of hydrogen fluoride maintained at −20° C., 133 milli-moles of butyne-2 was gradually added and the temperature of the mixture was slowly elevated over a period of 1 hour, and the reaction was carried out at room temperature for 10 minutes.

After the completion of the reaction, hydrogen fluoride was removed from the the reaction mixture and the product was purified by distillation to give 70 milli-moles of 2,2-difluorobutane having a purity of 98%.

EXAMPLE 1

A stainless steel reactor having an inner volume of 150 ml was charged with 200 milli-moles of CoF$_3$, and then 3 milli-moles of the 2,2-difluorobutane prepared in the referential example was added into the CoF$_3$ at a temperature of −196° C. The reactor was gradually heated and maintained at 50° C. for 1 hour.

Hydrogen fluoride (by-product) was removed from the reaction mixture and the product was purified by distillation to give 2,2,3-trifluorobutane having a purity of 83% in a yield of 76%.

The purity was determined by the gas chromatography and the yield was calculated from the results of the $^{19}$F-NMR and the gas chromatography. The 2,2,3-trifluorobutane was identified by the analyses of $^{19}$F-NMR, $^1$H-NMR and GC-MS.

EXAMPLES 2–5

By the same procedures described in Example 1, the reaction was carried out and the trifluorohydrocarbon compounds were separated wherein the reaction conditions described in Table 1 were employed. The purities and yields of the trifluorohydrocarbon compounds are shown in Table 1.

Thus, the trifluorohydrocarbon compounds could be obtained with high purity and in high yield.

1. A process for preparing a trifluorohydrocarbon compound represented by the following formula (2):

wherein R is an alkyl group having 1 to 4 carbon atoms, and each of R' and R" is a hydrogen atom, a halogen atom, or an alkyl group having 1 to 4 carbon atoms, which may have a halogen substituent, which comprises the step of reacting a difluorohydrocarbon compound represented by the following formula (1):

wherein R, R', and R" are as defined above, and are identical in formula (1) and formula (2), with cobalt trifluoride.

2. The process for preparing a trifluorohydrocarbon compound as claimed in claim 1, wherein the reaction is carried out at a temperature not higher than 150° C.

3. The process for preparing a trifluorohydrocarbon compound as claimed in claim 1, wherein the reaction is carried out at a temperature of −50° C. to 100° C.

4. The process for preparing a trifluorohydrocarbon compound as claimed in claim 1, wherein the reaction is carried out in the liquid phase.

5. The process for preparing a trifluorohydrocarbon compound as claimed in claim 1, wherein the reaction is carried out in a batchwise manner or a continuous manner.

6. The process for preparing a trifluorohydrocarbon compound as claimed in claim 1, wherein the reaction is carried out for 10 minutes to 5 days.

7. The process for preparing a trifluorohydrocarbon

TABLE 1

| Example No. | 2 | 3 | 4 | 5 |
|---|---|---|---|---|
| Starting difluorohydrocarbon compound and its amount (milli-moles) | CH$_3$—CF$_2$—CH$_2$CH$_3$<br>20 | CH$_3$—CF$_2$—CH$_3$<br>22 | CH$_3$—CF$_2$—CH$_2$CH$_2$CH$_3$<br>3 | CH$_3$—CF$_2$—CH$_2$Cl<br>3 |
| Reaction temperature (°C.) | 40 | 25 | 25 | 25 |
| Reaction time | 1 hour | 4 days | 2 hours | 4 days |
| Produced trifluorohydrocarbon compound | CH$_3$—CF$_2$—CHCH$_3$<br>F | CH$_3$—CF$_2$—CH$_2$F | CH$_3$—CF$_2$—CHCH$_2$CH$_3$<br>F | CH$_3$—CF$_2$—CHCl<br>F |
| Yield (%) | 84 | 85 | 67 | 50 |
| Purity (%) | 89 | 90 | 75 | 54 |

Industrial Applicability

The trifluorohydrocarbon compounds of the formula (2) prepared by the process of the present invention are useful as raw materials and intermediates for the synthesis of medicines and pesticides, detergents and solvents, and substitutes for Freons ®.

We claim:

compound as claimed in claim 1, wherein the amount of cobalt trifluoride is at least 2 moles per mole of the difluorohydrocarbon compound.

8. The process for preparing a trifluorohydrocarbon compound as claimed in claim 1, wherein the amount of cobalt trifluoride is 2 to 200 moles per mole of the difluorohydrocarbon compound.

9. The process for preparing a trifluorohydrocarbon compound as claimed in claim 4, wherein the reaction is

PROCESS FOR PREPARING TRIFLUOROHYDROCARBON COMPOUND

BACKGROUND OF THE INVENTION

1. Technical Field of the Invention

This invention relates to a process for preparing a trifluorohydrocarbon compound.

2. Background Art

Various fluorine-containing compounds have heretofore been used as medicines, pesticides, detergents and solvents, and as raw materials and intermediates used for the preparation of these materials.

In recent years, to cope with an environmental problem of depletion of the ozone layer caused by Freon ® compounds, especially chlorofluorocarbons, other fluorine-containing compounds have been intensively investigated and developed as substitutes for Freon compounds.

A process is known for preparing the fluorine-containing compounds having a high practical use, which comprises converting a carbon-hydrogen bond of a hydrocarbon compound to a carbon-fluorine bond by using cobalt trifluoride ($CoF_3$) [see, for example, R. E. Banks, J. C. Tatlow, J. Fluorine Chem., 33, 227(1986)].

However, there are no great differences among the reactivities of the plurality of carbon-hydrogen bonds in the hydrocarbon compound used as the raw material, and therefore, a mixture of various fluorinated compounds having one or more bonded fluorine atoms or many isomers are inevitably produced. In other words, the fluorination reaction is not selective. Thus, a process for selectively fluorinating hydrocarbon compounds by using a cobalt trifluoride is not known.

SUMMARY OF THE INVENTION

In view of the foregoing state of art, an object of the present invention is to solve the problems of the conventional process, and to provide a process by which a fluorine-containing compound can be efficiently prepared with high selectivity.

More specifically, an object of the present invention is to provide a process for the preparation of a fluorine-containing compound wherein a gem-difluorohydrocarbon compound is capable of being partially fluorinated under mild reaction conditions with high selectivity.

In accordance with the present invention, there is provided a process for preparing a trifluorohydrocarbon compound represented by the following formula (2):

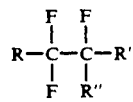

wherein R is an alkyl group having 1 to 4 carbon atoms, and each of R' and R" is a hydrogen atom, a halogen atom or an alkyl group having 1 to 4 carbon atom, which may have a halogen substituent, which comprises the step of reacting a difluorohydrocarbon compound represented by the following formula (1):

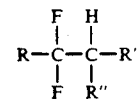

wherein R, R' and R" are as defined above, with cobalt trifluoride.

DETAILED DESCRIPTION OF THE INVENTION

The starting compound used in the process of the present invention is a difluorohydrocarbon compound which is represented by the above formula (1), wherein R is an alkyl group having 1 to 4 carbon atoms, and each of R' and R" is a hydrogen atom, a halogen atom or an alkyl group having 1 to 4 carbon atom, which may have a halogen substituent. As the alkyl groups, there can be mentioned, for example, a methyl group, an ethyl group, an isopropyl group, a butyl group and an isobutyl group. As the halogen atom, there can be mentioned, for example, a chlorine atom and a bromine atom. As specific examples of the difluorohydrocarbon compound of the formula (1), there can be mentioned 2,2-difluoropropane, 2,2-difluorobutane, 2,2-difluoropentane, 3,3-difluoropentane, 2,2-difluoro-1-chloropropane, 2,2-difluoro-1,1-dichloropropane, 3,3-difluoro-1-chlorobutane and 3,3-difluoro-1-chloropentane.

These difluorohydrocarbon compounds of the formula (1) can be prepared by known procedures. For example, there can be mentioned a process wherein a corresponding acetylene compound is reacted with hydrogen fluoride (HF), a process wherein a corresponding carbonyl compound is reacted with a fluorinating agent such as $SF_4$, and a process wherein a corresponding dichlorohydrocarbon compound is reacted with $SbF_4$.

The reaction of the difluorohydrocarbon of the formula (1) with cobalt trifluoride ($CoF_3$) is carried out at a temperature not higher than 150° C., preferably 100° C. to −50° C. Where the temperature exceeds 150° C., a non-selective fluorination reaction may occur. Therefore, it is preferable that the temperature is gradually elevated and the reaction is carried out at the above-mentioned low temperature.

The reaction may be carried out either in the liquid or gaseous phase, and either in a batchwise manner or a continuous manner. The reation time is not particularly limited, but is usually in the range of about 10 minutes to about 5 days. The proportion of cobalt trifluoride to the difluorohydrocarbon is such that the amount of cobalt trifluoride is at least 2 moles, preferably 2 to about 200 moles, per mole of the difluorohydrocarbon compound.

When the reaction is carried out in the liquid phase, a liquid medium may be used. The liquid medium used is not particularly limited, and halogenated hydrocarbon liquid media such as carbon tetrachloride, dichlorodifluoromethane and trichlorofluoromethane are preferably used.

By reacting the difluorohydrocarbon compound with cobalt trifluoride under the above-mentioned conditions, the gem-difluorohydrocarbon compound can be selectively and partially fluorinated under mild conditions to yield the trifluorohydrocarbon compound of the formula (2) at a high efficiency.

The process for the preparation of the trifluorohydrocarbon compound in accordance with the present carried out in the liquid phase by using a halogenated hydrocarbon liquid medium.

10. The process for preparing a trifluorohydrocarbon compound as claimed in claim 1, wherein the reaction is carried out in the gaseous phase.

11. The process for preparing a trifluorohydrocarbon compound as claimed in claim 1, wherein the reaction is carried out in a continuous manner.

* * * * *